(12) United States Patent
Godek et al.

(10) Patent No.: US 11,426,411 B2
(45) Date of Patent: *Aug. 30, 2022

(54) CYCLOALKYL-DIAMINES FOR THE TREATMENT OF INFLAMMATION

(71) Applicants: Dennis Michael Godek, Glastonbury, CT (US); Harry Ralph Howard, Bristol, CT (US); Andrew Morgan Stewart, East Lyme, CT (US)

(72) Inventors: Dennis Michael Godek, Glastonbury, CT (US); Harry Ralph Howard, Bristol, CT (US); Andrew Morgan Stewart, East Lyme, CT (US)

(73) Assignee: MediSynergics, LLC, Farmington, CT (US)

( * ) Notice: Subject to any disclaimer, the term of this patent is extended or adjusted under 35 U.S.C. 154(b) by 251 days.

This patent is subject to a terminal disclaimer.

(21) Appl. No.: 16/997,146

(22) Filed: Aug. 19, 2020

(65) Prior Publication Data

US 2021/0060023 A1 Mar. 4, 2021

Related U.S. Application Data

(63) Continuation-in-part of application No. 16/880,416, filed on May 21, 2020, now Pat. No. 11,007,200.

(60) Provisional application No. 62/889,801, filed on Aug. 21, 2019.

(51) Int. Cl.
| | |
|---|---|
| *A61K 31/5375* | (2006.01) |
| *A61K 31/40* | (2006.01) |
| *A61K 31/439* | (2006.01) |
| *A61K 31/415* | (2006.01) |
| *A61K 31/495* | (2006.01) |
| *C07C 221/00* | (2006.01) |
| *C07C 249/02* | (2006.01) |

(52) U.S. Cl.
CPC .......... *A61K 31/5375* (2013.01); *A61K 31/40* (2013.01); *A61K 31/415* (2013.01); *A61K 31/439* (2013.01); *A61K 31/495* (2013.01)

(58) Field of Classification Search
None
See application file for complete search history.

(56) References Cited

U.S. PATENT DOCUMENTS

| 11,007,200 B2* | 5/2021 | Godek | ............... A61K 31/5375 |
| 2015/0210626 A1* | 7/2015 | Godek | ............... A61K 31/4164 |
| | | | 514/357 |
| 2016/0101068 A1* | 4/2016 | Godek | .................. C07C 217/08 |
| | | | 514/408 |
| 2016/0151308 A1* | 6/2016 | Godek | ................. A61K 31/495 |
| | | | 514/357 |

* cited by examiner

*Primary Examiner* — Amanda L. Aguirre

(57) ABSTRACT

The invention is directed to a method of treatment for inflammation in mammals including inflammation caused by bacterial or viral infection, the method comprising administering to a mammal, including a human, in need of such treatment a therapeutically effective amount of a compound of formula I, or a pharmaceutically acceptable salt thereof.

12 Claims, No Drawings

CYCLOALKYL-DIAMINES FOR THE TREATMENT OF INFLAMMATION

This patent application claims the benefit of U.S. Provisional Application Ser. No. 62/889,801, filed Aug. 21, 2019.

BACKGROUND OF THE INVENTION

This invention is directed to a method of use for the treatment of inflammation in a mammal, comprising the administration of a therapeutically effective amount of a compound of formula I, of a pharmaceutically acceptable salt thereof, and a pharmaceutically acceptable carrier.

Inflammation is the body's biological response to harmful stimuli (e.g., pathogens, irritants and the like) and is designed to be protective. It is a mechanism by which the body attempts to eliminate the initial cause(s) of cell injury or tissue damage, as well as an attempt to initiate tissue repair. Inflammation can be of short duration (i.e., acute) or long-lasting (i.e., chronic). Acute inflammation may subside within hours or days. Chronic inflammation can persist and produce mild to severe, non-remitting pain that lasts for months or years, even after the causative agent has been eliminated. The associated pain may be localized at the site of an infection or may be referred from a more distant location in the body, often making the diagnosis and treatment of the specific pain more difficult. Conditions and diseases often linked to chronic inflammation include cancer, heart disease, diabetes, asthma and Alzheimer's disease, to name a few.

Recently, there has been increased awareness of the therapeutic potential of novel compounds which function as Sigma-2 (σ2) receptor ligands. The structure and functions of this "receptor", which has been defined in the literature as a "chaperone protein", have been described in a variety of scientific publications including, e.g., G Duncan, L Wang, et al (2005) *Experimental Eye Research,* 81:121-122; J L Ortega-Roldan, F Ossa, J R Schnell (2013) *Journal of Biological Chemistry,* 288(29):21448-21457; F P Monnet (2005) *Biology of the Cell,* 97:873-883 (doi:10.1042/BC20040149); M Ishikawa, K Hashimoto (2010) *Journal of Receptor, Ligand and Channel Research,* 3:25-36; J Sahn, G L Meija, P R Ray, S P Martin, T J Price, "Sigma 2 Receptor/Tmem97 Agonists Produce Long Lasting Antineuropathic Pain Effects in Mice" (2017) *ACH Chem Neurosci* 8(8):1801-1811). Compounds with Sigma-2 activity have also been reported to be potentially useful for the treatment of neuropsychiatric disorders (e.g., schizophrenia) and a variety of cancers ("Sigma-2 Receptor"; URL: https://en.wikipedia.org/wiki/Sigma-2_receptor).

A growing number of recent publications now provide additional scientific rationale and evidence that such compounds may have therapeutic potential for antibacterial and antiviral activity, reducing or eliminating the source of inflammation caused by proinflammatory cytokines such as IL-6 (i.e., Interleukin-6) and TNF-α (i.e., Tumor Necrosis Factor alpha) that arise when humans are exposed to these organisms. A recent publication by D. Gordon identifies two sets of therapeutic agents that have displayed SARS-CoV-2 antiviral activity. One of these drug classes binds with high affinity to the Sigma-1 or Sigma-2 receptor proteins (D Gordon, G M Jang, M Bouhaddou, J Xu, K Obernier, K M White, et al, "A SARS-CoV-2 protein interaction map reveals targets for drug repurposing", *Nature,* published on Apr. 30, 2020), suggesting a possible role for such drugs in the treatment of this highly contagious coronavirus.

It is further documented in the scientific literature that ketamine, a sedative and anesthesia-inducing drug, also has preclinical and clinical antiinflammatory efficacy in the regulation of inflammatory cytokines, including IL-6 and TNF-α. IL-6 has been identified as a proinflammatory cytokine target in the treatment of ARDS (Acute Respiratory Distress Syndrome) which develops in some patients diagnosed with the coronavirus responsible for SARS-CoV-2. Surgeons and anesthesiologists have used ketamine in treating their surgical patients because they often experience reduced inflammation during post-operative treatment and report better recovery outcomes. (M. D. Kock, et al "Ketamine and Peripheral Inflammation", (2013) *CNS Neuroscience & Therapeutics* 19:403-410. Also see: O. Dale, et al "Does Intraoperative Ketamine Attenuate Inflammatory Reactivity Following Surgery? A Systematic Review and Meta-Analysis" (2012) *Anesthesia & Analgesia* 115(4): 934-943; Q Chen, J Feng, X Wang, et al, "The effect of ketamine on microglia and pro-inflammatory cytokines in the hippocampus of depression-like rat", (2017) *Neuropsychiatry (London)* 7(2):77-85; KW Suhs, V Gudi, N Ekermann, R Fairless, et al, "Cytokine regulation by modulation of the NMDA receptor on astrocytes", (2016) Neuroscience Letters 227-233; and Y Li, R Shen, G Wen, R Ding, et al, "Effects of Ketamine on Levels of Inflammatory Cytokines IL-6, IL-1β, and TNF-α in the Hippocam pus of Mice Following Acute or Chronic Administration", (2017) *Frontiers in Pharmacology* Vol 8, Article 139).

The SARS-CoV-2 virus has been reported to target the Central Nervous System (CNS), as indicated by the loss of smell and taste in some patients, which may further support the use of ketamine and ketamine-derived compounds. A June 2020 publication in *Emerging Infectious Diseases* (K Benameur, A Agarwal, S C Auld, M P Butters, A S, Webster T Ozturk, et al, "Encephalopathy and encephalitis associated with cerebrospinal fluid cytokine alterations and coronavirus disease", (2020) *Emerg. Infect. Dis.* September (https://doi.org/10.3201/eid2609.202122)) found virus antibodies in the cerebral spinal fluid (CSF) of a small group of patients, supporting the reports of evidence of brain exposure by the virus.

Researchers in South Korea have previously published a natural products paper that describes the isolation and identification of compounds with structures similar to compounds of the current patent application, demonstrating inhibition of proinflammatory cytokines IL-6 and TNF-α in lung inflammation. (H J Lim, et al, "Inhibition of Proinflammatory Cytokine Generation in Lung Inflammation by the Leaves of *Perilla frutescens* and its Constituents", (2014) *Biomolecules & Therapeutics* 22(1) 62-67).

Furthermore, the Sigma-1 receptor has been highlighted in a recent publication describing a method for controlling bacterial-induced inflammation and sepsis in preclinical models with the antidepressant fluvoxamine. (D A Rosen, et al, "Modulation of the sigma-1 receptor-IRE1 pathway is beneficial in preclinical models of inflammation and sepsis", (2019) *Science Translational Medicine,* 11, eaau5266.

Of particular interest to MediSynergics, LLC is the discovery of new, safe therapies for reducing inflammation in humans and in other mammals. The ketamine-derived compounds disclosed in the present application have demonstrated potent Sigma-1 and/or Sigma-2 binding affinities (Ki), often below 100 nM for these receptors, as well as selectivity over other receptors associated with inflammation.

MediSynergics, LLC (MS) has previously disclosed the use of cycloalkyl-diamines derived from ketamine for a variety of human and animal disorders. These include parasitic diseases such as trypanosomiasis ("Cycloalkyl Diamines", U.S. Pat. No. 9,126,891, issued Sep. 8, 2015), psychiatric disorders such as depression and schizophrenia ("Cycloalkyl-diamines for CNS Disorders", U.S. Pat. No. 9,283,196, issued Mar. 15, 2016), cancer ("Anti-cancer Cycloalkyl Diamines", U.S. Pat. No. 9,345,673, issued May 24, 2016) and amyotrophic lateral sclerosis, or ALS ("Cycloalky-diamines for Neurodegenerative Disorders", U.S. Pat. No. 9,381,170, issued Jul. 5, 2016). More recently, MS has disclosed the potential use of such compounds as treatments for pain disorders ("Cycloalkyl-Diamines for the Treatment of Pain", U.S. Provisional patent application 62/889,801, filed Aug. 21, 2019 and the corresponding U.S. Non-Provisional patent application Ser. No. 16/880,416, filed May 21, 2020. This current patent application is a Continuation-In-Part (CIP) of said Non-Provisional application.

The present invention relates to the use of novel cycloalkyl-diamines of structural formula I and to their pharmaceutical compositions in the treatment of inflammation and inflammatory disorders in mammals, including humans. In particular, it relates to the use of compounds of the general formula I and their use in the treatment of bacterial or viral infections.

SUMMARY OF THE INVENTION

The present invention is directed to a method for the treatment of inflammation and inflammatory disease in a mammal, including a human, by administering a compound of the formula I, or a pharmaceutically effective salt(s) thereof, in an amount which is effective at reducing or eliminating pain in said mammal, wherein:

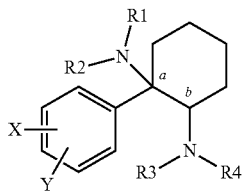

I

X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(C=O)—R5, NH—(C=O)—R5, —NR5—(C=O)—R6, —(C=O)—NHR5 and —(C=O)—NR5R6;

R1 is hydrogen:
R2 is hydrogen or $C_1$-$C_6$-alkyl:
R3 is hydrogen or $C_1$-$C_6$-alkyl:
R4 is selected from the group consisting of $C_1$-$C_6$-alkyl, $C_3$-$C_7$-cycloalkyl, $(CH_2)_n$—R7, or NR3N4 is a 5- to 12-membered cyclic or bicyclic ring system containing up to two additional heteroatoms in the rings selected from N, O and S;

R5 is selected from $C_1$-$C_6$-alkyl and aryl;
R6 is selected from $C_1$-$C_6$-alkyl and aryl; or NR5R6 is a 5- to 12-membered cyclic or bicyclic ring system containing up to two additional heteroatoms in the ring, selected from N, O and S;

R7 is independently selected from the group consisting of H, $C_1$-$C_6$-alkyl, $C_3$-$C_7$-cycloalkyl, ($C_1$-$C_6$-alkoxy)-, ($C_1$-$C_6$-alkoxy)-($C_1$-$C_6$-alkyl), NR8R9, NR8R9-($C_1$-$C_6$-alkyl), aryl, heterocyclyl and heteroaryl;

R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S;

N is an integer between 1 and 6, and
"a" and "b" denote chiral carbon centers.
Preferred embodiments of the present invention include the compounds of formula I in which:
(A) R2 is methyl, R1 and R3 are hydrogen, y is hydrogen:
X is halogen;
N is an integer between 0 and 6; and
R7 is aryl or heteroaryl.
(B) R2 is methyl, R1 and R3 are hydrogen; Y is hydrogen;
X is halogen;
N is an integer between 0 and 6; and
R7 is heterocyclyl.
(C) R2 is methyl, R1 and R3 are hydrogen; Y is hydrogen;
X is halogen;
N is an integer between 0 and 6; and
R7 is NR8R9.

Preferred compounds of formula I in accordance with the present invention include:
Cis-(1S,2S)-1-(2-chlorophenyl)-$N^1$-methyl-$N^2$-[3-(pyrrolidin-1-yl)propyl]-cyclohexane-1,2-diamine trihydrochloride;
Trans-(1S,2R)-1-(2-chlorophenyl)-$N^1$-methyl-$N^2$-[3-(pyrrolidin-1-yl)propyl]-cyclohexane-1,2-diamine trihydrochloride;
Cis-(1S,2S)-1-(2-chlorophenyl)-$N^2$-[3-(4-fluorophenyl)propyl]-$N^1$-methylcyclohexane-1,2-diamine dihydrochloride;
Trans-(1S,2R)-1-(2-chlorophenyl)-$N^2$-[3-(4-fluorophenyl) propyl]-$N^1$-methylcyclohexane-1,2-diamine dihydrochloride;
Cis-(1S,2S)-1-(2-chlorophenyl)-$N^1$-methyl-$N^2$-(3-phenylpropyl)cyclohexane-1,2-diamine dihydrochloride;
Trans-(1S,2R)-1-(2-chlorophenyl)-$N^1$-methyl-$N^2$-(3-phenylpropyl)cyclohexane-1,2-diamine dihydrochloride;
Cis-(1S,2S)-1-(2-chlorophenyl)-$N^2$-(3,4-dimethoxyphenethyl)-$N^1$-methylcyclohexane-1,2-diamine dihydrochloride;
Trans-(1S,2R)-1-(2-chlorophenyl)-$N^1$-(3,4-dimethoxyphenethyl)-$N^1$-methylcyclohexane-1,2-diamine dihydrochloride;
Cis-(1S,2S)-1-(2-chlorophenyl)-$N^1$-methyl-$N^2$-(3-morpholinopropyl)cyclohexane-1,2-triamine dihydrochloride;
Trans-(1S,2R)-1-(2-chlorophenyl)-$N^1$-methyl-$N^2$-(3-morpholinopropyl)cyclohexane-1,2-triamine dihydrochloride;
Cis-(1R,2S)—$N^2$-benzyl-1-(2-chlorophenyl)-$N^1$-methylcyclohexane-1,2-diamine dihydrochloride;
Trans-(1R,2R)—$N^2$-benzyl-1-(2-chlorophenyl)-$N^1$-methylcyclohexane-1,2-diamine dihydrochloride;
Cis-(1S,2R)—$N^2$-benzyl-1-(2-chlorophenyl)-$N^1$-methylcyclohexane-1,2-diamine dihydrochloride;
Trans-(1S,2S)—$N^2$-benzyl-1-(2-chlorophenyl)-$N^1$-methylcyclohexane-1,2-diamine dihydrochloride;
Cis-(1R,2S)-1-(2-chlorophenyl)-$N^1$-methyl-$N^2$-[3-(pyrrolidin-1-yl)propyl]-cyclohexane-1,2-diamine trihydrochloride;
Trans-(1R,2R)-1-(2-chlorophenyl)-$N^1$-methyl-$N^2$-[3-(pyrrolidin-1-yl)propyl]-cyclohexane-1,2-diamine trihydrochloride;

Cis-(1R,2S)-1-(2-chlorophenyl)-$N^2$-(3,4-dimethoxyphenethyl)-$N^1$-methylcyclohexane-1,2-diamine dihydrochloride;
Trans-(1R,2R)-1-(2-chlorophenyl)-$N^2$-(3,4-dimethoxyphenethyl)-$N^1$-methyl-cyclohexane-1,2-diamine dihydrochloride;
Cis-(1S,2S)-1-(2-chlorophenyl)-$N^2$-(3,4-dichlorobenzyl)-$N^1$-methylcyclohexane-1,2-diamine dihydrochloride;
Trans-(1S,2R)-1-(2-chlorophenyl)-$N^2$-(3,4-dichlorobenzyl)-$N^1$-methylcyclohexane-1,2-diamine dihydrochloride;
Cis-(1S,2S)—$N^2$-(3-aminopropyl)-1-(2-chlorophenyl)-$N^1$-methylcyclohexane-1,2-diamine trihydrochloride;
Trans-(1S,2R)—$N^2$-(3-aminopropyl)-1-(2-chlorophenyl)-$N^1$-methylcyclohexane-1,2-diamine trihydrochloride;
(1S,2S)-1-(2-chlorophenyl)-$N^1$-methyl-$N^2$-(3-(4-methylpiperazin-1-yl)propyl)-cyclohexane-1,2-diamine tetrahydrochloride; and
(1S,2R)-1-(2-chlorophenyl)-$N^1$-methyl-$N^2$-(3-(4-methylpiperazin-1-yl)propyl)-cyclohexane-1,2-diamine tetrahydrochloride.

Other compounds of the invention will include, but are not limited to:
(1R,2S)-1-(2-chlorophenyl)-$N^1$-methyl-$N^2$-(3-(pyrrolidin-1-yl)propyl)cyclohexane-1,2-diamine;
(1R,2S)—$N^2$-(3-(1H-pyrrol-1-yl)propyl)-1-(2-chlorophenyl)-$N^1$-methylcyclohexane-1,2-diamine;
(1R,2S)-1-(2-chlorophenyl)-$N^1$-methyl-$N^2$-(3-(2-methyl-1H-imidazol-1-yl)-propyl)cyclohexane-1,2-diamine;
(1R,2S)-1-(2-chlorophenyl)-$N^1$-methyl-$N^2$-(3-(4-methylpiperazin-1-yl)propyl)-cyclohexane-1,2-diamine;
(1R,2S)-1-(2-chlorophenyl)-$N^1$-methyl-$N^2$-(3-morpholinopropyl)cyclohexane-1,2-diamine;
(1R,2S)-1-2-chlorophenyl)-$N^1$-methyl-$N^2$-(3-(pyrrolidine-1-yl)propyl)-cyclohexane-1,2-diamine;
(1R,2S)-1-(2-chlorophenyl)-$N^2$-(3-(dimethylamino(propyl)-$N^1$-methylcyclohexane-1,2-diamine;
(1R,2S)—$N^2$-(1-chlorobenzyl)-1-(2-chlorophenyl)-$N^1$-methylcyclohexane-1,2-diamine;
(1R,2S)-(2-chlorophenyl)-$N^2$-(3,5-difluorobenzyl)-$N^1$-methylcyclohexane-1,2-diamine;
(1R,2S)-1-(2-chlorophenyl)-$N^1$-methyl-$N^2$-(4-(trifluoromethyl)benzyl)-cyclohexane-1,2-diamine;
(1R,2S)-1-(2-chlorophenyl)-$N^1$-methyl-$N^2$-(4-((trifluoromethyl)thio)benzyl)-cyclohexane-1,2-diamine;
(1R,2S)—$N^2$-(5-chloro-2-fluorobenzyl)-1-(2-chlorophenyl)-$N^1$-methylcyclohexane-1,2-diamine;
(1R,2S)-1-(2-chlorophenyl)-$N^2$-(5-methoxy-2-methylbenzyl)-$N^1$-methylcyclohexane-1,2-diamine:
(1R,2S)-1-(2-chlorophenyl)-$N^1$-methyl-$N^2$-(thiazol-2-ylmethyl)cyclohexane-1,2-diamine;
(1R,2S)-1-(2-chlorophenyl)-$N^1$-methyl-$N^2$-(thiophen-3-ylmethyl)cyclohexane-1,2-diamine;
(1R,2S)-1-(2-chlorophenyl)-$N^2$-(furan-2-ylmethyl)-$N^1$-methylcyclohexane-1,2-diamine;
(1R,2S)-1-(2-chlorophenyl)-$N^1$-methyl-$N^2$-(thiophen-2-ylmethyl)cyclohexane-1,2-diamine;
(1R,2S)-1-(2-chlorophenyl)-$N^1$-methyl-$N^2$-((methyl-1H-pyrazol-4-yl)methyl)-cyclohexane-1,2-diamine;
(1R,2S)-1-(2-chlorophenyl)-$N^2$-(cyclobutylmethyl)-$N^1$-methylcyclohexane-1,2-diamine;
(1R,2S)-1-(2-chlorophenyl)-$N^2$-(cyclopropylmethyl)-$N^1$-methylcyclohexane-1,2-diamine;
(1R,2S)-1-(2-chlorophenyl)-$N^1$-methyl-$N^2$-neopentylcyclohexane-1,2-diamine;
(1R,2S)-1-(2-chlorophenyl)-$N^2$-(2,2-difluoroethyl)-$N^1$-methylcyclohexane-1,2-diamine;
(1R,2S)-1-(2-chlorophenyl)-$N^2$-(cyclopropylethyl)-$N^1$-methylcycohexane-1,2-diamine;
(1R,2S)-1-(2-chlorophenyl)-$N^2$-cyclohexylmethyl)-$N^1$-methylcyclohexane-1,2-diamine;
(1R,2S)-1-(2-chlorophenyl)-$N^1$-methyl-$N^2$—((R))-quinuclidin-3-yl)cyclohexane-1,2-diamine:
(1R,2S)-1-(2-chlorophenyl)-$N^1$-methyl-$N^2$—((S)-quinuclidin-3-yl)cyclohexane-1,2-diamine:
(1R,2S)-1-(2-chlorophenyl)-$N^1$-methyl-$N^2$-(pyridine-4-ylmethyl)cyclohexane-1,2-diamine:
(1R,2S)-1-(2-chlorophenyl)-$N^1$-methyl-$N^2$-(pyridine-2-ylmethyl)cyclohexane-1,2-diamine;
(1R,2S)-1-(2-chlorophenyl)-$N^1$-methyl-$N^2$-(pyrimidin-2-ylmethyl)cyclohexane-1,2-diamine;
(1R,2S)-1-(2-chlorophenyl)-$N^1$-methyl-$N^2$-(3-methylpyridin-4-yl)methyl)-cyclohexane-1,2-diamine;
(1R,2S)-1-(2-chlorophenyl)-$N^1$-methyl-$N^2$-(pyrazin-2-ylmethyl)cyclohexane-1,2-diamine;
(1R,2S)-1-(2-chlorophenyl)-$N^1$-methyl-$N^2$-(quinoline-6-ylmethyl)cyclohexane-1,2-diamine;
(1R,2S)-1-(2-chlorophenyl)-$N^1$-methyl-$N^2$-((1-methyl-1H-indol-5-yl)methyl)-cyclohexane-1,2-diamine;
(1R,2S)-1-(2-chlorophenyl)-$N^2$—((S)-1-(4-methoxyphenyl)ethyl)-$N^1$-methylcyclohexane-1,2-diamine;
(1R,2S)-1-(2-chlorophenyl)-$N^{2)}$-1-(4-methoxyphenyl)ethyl)-$N^1$-methylcyclohexaane-1,2-diamine;
(1R,2S)-1-(2-chlorophenyl)-$N^1$-methyl-$N^2$—((S)-1-phenylethyl)cyclohexane-1,2-diamine;
(1R,2S)-1-(2-chlorophenyl)-$N^1$-methyl-$N^{2)}$-1-phenylethyl)cyclohexane-1,2-diamine;
(1R,2S)-1-(2-chlorophenyl)-$N^1$-methyl-$N^2$—((S)-1-(p-tolylethyl)cyclohexane-1,2-diamine;
(1R,2S)-1-(2-chlorophenyl)-$N^1$-methyl-$N^{2)}$-1-(p-tolylethyl)cyclohexane-1,2-diamine;
(1R,2S)-1-(2-chlorophenyl)-$N^1$-methyl-$N^2$—((S)-2-phenylpropyl)cyclohexane-1,2-diamine:
(1R,2S)-1-(2-chlorophenyl)-$N^1$-methyl-$N^{2)}$-2-phenylpropyl)cyclohexane-1,2-diamine;
(1R,2S)-1-(2-chlorophenyl)-$N^1$-methyl-$N^2$—((S)-1-(p-tolyl)ethyl)cyclohexane-1,2-diamine;
(1R,2S)-1-(2-chlorophenyl)-$N^1$-methyl-$N^{2R)-N)}$-1-(p-tolyl)ethyl)cyclohexane-1,2-diamine;
(R)-1-((1S,2R)-2-(2-chlorophenyl)-2-(methylamino)cyclohexyl)-N,N-dimethylpyrrolidin-3-amine; and
(S)-1-((1S,2R)-2-(2-chlorophenyl)-2-(methylamino)cyclohexyl)-N,N-dimethylpyrrolidin-3-amine.

DETAILED DESCRIPTION OF THE INVENTION

The compounds of formula I may be prepared as described in the following reaction schemes and discussions. Unless otherwise indicated, X, Y, R1, R2, R3, R4, R5, R6, R7 and structural formulae II, III, IV, V, VI, VII, VIII, IX, X, XI, XII, XIII, XIV and XV in the reaction schemes and discussion that follow are defined as above.

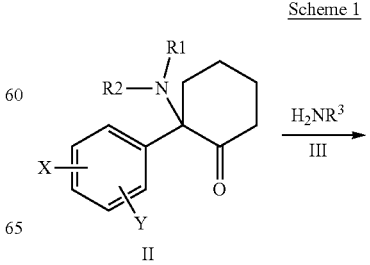

Scheme 1

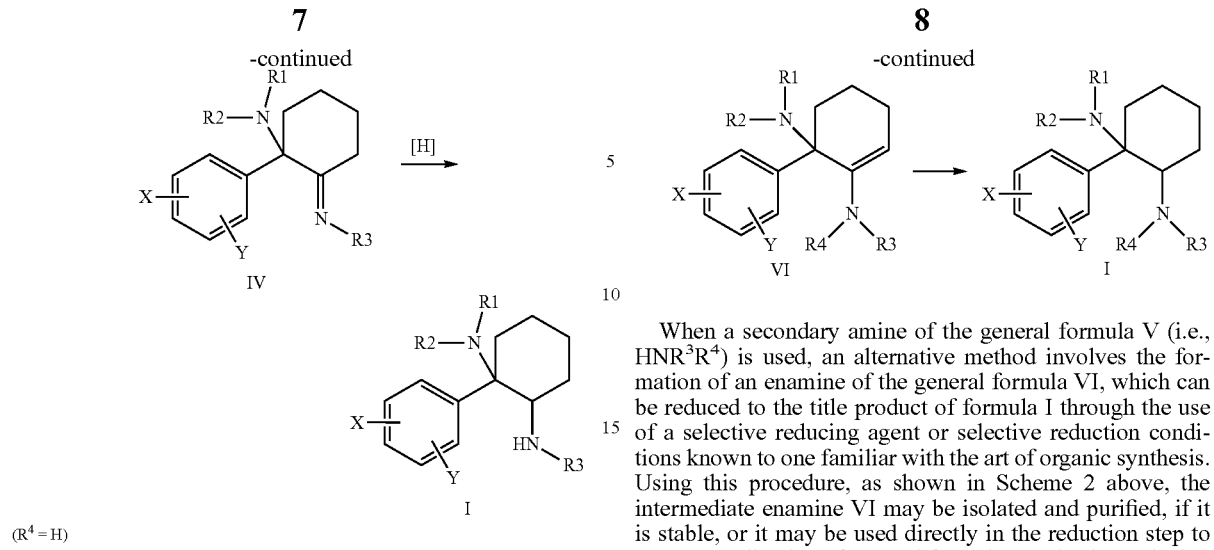

(R⁴ = H)

According to Scheme 1, a ketone of the general formula II, wherein X, Y, R1 and R2 are as previously defined, may be converted directly into the corresponding compound of the formula I, via an intermediate of the general formula IV, by reacting it with one or more equivalents of a primary amine of the general formula III in the presence of a reducing reagent. Reducing reagents that may be used include sodium cyanoborohydride, sodium triacetoxyborohydride, sodium borohydride, lithium aluminum hydride, hydrogen gas and a metal catalyst, or zinc plus hydrochloric acid. This reaction is typically conducted in a reaction inert solvent at a temperature from about 0° C. to about 150° C., but may be conducted in the absence of solvent. Suitable reaction inert solvents include lower alcohols (e.g., methanol, ethanol, isopropanol), 1,2-dichloroethane, acetic acid or tetrahydrofuran. Preferably the reaction is conducted with an excess of the corresponding amine III, in the absence of additional solvent, at a temperature of about 110° C. and using the reducing agent sodium cyanoborohydride.

Alternatively, the reaction of a compound of formula II with an amine compound of the formula III may be carried out in the presence of a dehydrating agent (e.g., titanium tetrachloride) or by using an apparatus designed to azeotropically remove the water generated, to produce an imine of the formula IV. This imine may then be converted to the title product of formula I by reduction of the C=N double bond with a reducing agent as described above, preferably with sodium cyanoborohydride in the presence or absence of a suitable, reaction inert solvent as described in the preceding paragraph at a temperature of about 0° C. to about 150° C. and preferably at about 110° C. Other suitable dehydrating agent/solvent systems include titanium tetrachloride in dichloromethane, titanium isopropoxide in dichloromethane and activated molecular sieves in toluene or in dichloromethane.

Scheme 2

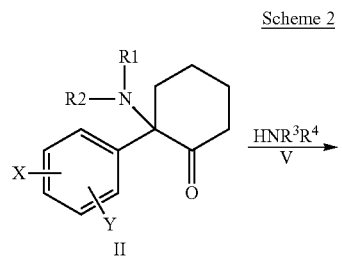

When a secondary amine of the general formula V (i.e., HNR³R⁴) is used, an alternative method involves the formation of an enamine of the general formula VI, which can be reduced to the title product of formula I through the use of a selective reducing agent or selective reduction conditions known to one familiar with the art of organic synthesis. Using this procedure, as shown in Scheme 2 above, the intermediate enamine VI may be isolated and purified, if it is stable, or it may be used directly in the reduction step to generate a diamine of general formula I. Selective reducing agents and reagents to facilitate the conversion of intermediate VI to the compounds of formula I include: formic acid, hydrogen gas and a metal catalyst (e.g., Pd metal on carbon, Pt metal on carbon).

In another method (Scheme 3, below) for the preparation of the compounds of the present invention, an intermediate oxime (VII) can be prepared through the reaction of the starting ketone 1 and hydroxylamine. Synthesis of such oximes is well precedented in the chemical literature (e.g., see J L LaMattina, et al, *Synthesis* (1980) 329-330). It is also known that intermediate oximes like VII are capable of forming two different isomers, denoted as Z- and E-oximes. These isomers may or may not react differently in the subsequent conversion to intermediates of general formula VIII (i.e., I, where R3, R4=H), and one of the oxime isomers may be less reactive or resistant to reduction to intermediate VIII. The reduction to VIII can be achieved using one of a variety of reagents and procedures, including Zn-Acetic acid, Na metal and ethanol, BH₃, and NaBH₃CN—TiCl₃.

Scheme 3

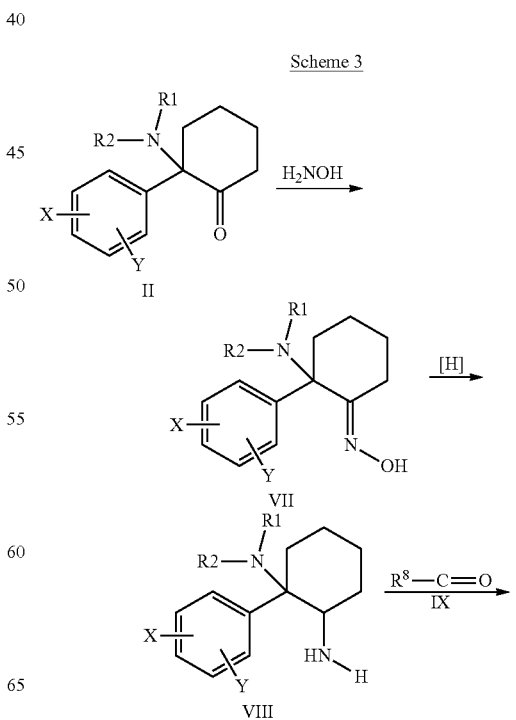

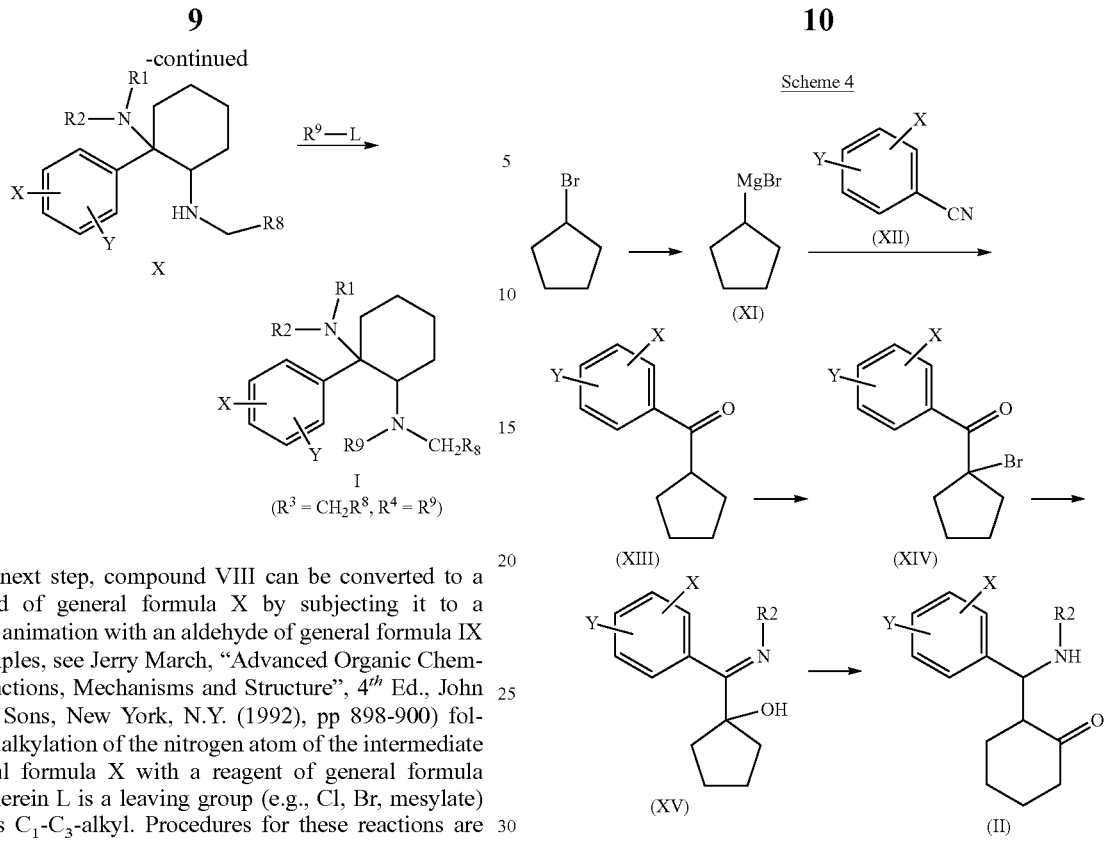

Scheme 4

In the next step, compound VIII can be converted to a compound of general formula X by subjecting it to a reductive amination with an aldehyde of general formula IX (for examples, see Jerry March, "Advanced Organic Chemistry: Reactions, Mechanisms and Structure", 4$^{th}$ Ed., John Wiley & Sons, New York, N.Y. (1992), pp 898-900) followed by alkylation of the nitrogen atom of the intermediate of general formula X with a reagent of general formula R9-L, wherein L is a leaving group (e.g., Cl, Br, mesylate) and R9 is $C_1$-$C_3$-alkyl. Procedures for these reactions are readily available in the chemical literature and familiar to chemists with skill in the art of organic synthesis.

The starting ketone for the above processes, compound II, may be obtained from commercial sources or may be synthesized as described in the chemical literature (Scheme 4). Such compounds may exist as racemic mixtures or as the individual (+)- and (−)-isomers. Ketamine (II, R1=CH$_3$, X=2-Cl, R2, Y=H) may be purchased from commercial sources as a mixture of R- and S-isomers. The S-isomer (i.e., esketamine) can also be obtained commercially, but the R-isomer is prohibitively expensive. The individual isomers are reportedly obtained through a resolution process (Y A Tawar, et al, "Process for Preparation of Substantially Optically Pure (R)- and (S)-Enantiomers of Ketamine and Its Pharmaceutical Acceptable Salts" (2017), *Parapex-Indian Journal of Research*, 6(1): 201-204. A modified process, with much improved yields and purity of the individual (R)- and (S)-enantiomers, is detailed in the experimental section that follows.

In general, 1-bromo-cyclopentane is converted to a Grignard reagent (XI) by reaction with magnesium metal in an inert solvent, typically in an ether like diethyl ether or tetrahydrofuran (THF). The Grignard reagent so formed is then reacted with an appropriately substituted aryl-nitrile (XII) in an inert solvent such as hexane, and stirred at room temperature until the reaction is determined to have been completed. The product, an aryl-ketone (XIII), dissolved in a suitable solvent (e.g., chloroform) is then treated with one equivalent of bromine (Br$_2$), and the resulting α-bromo-ketone (XIV) is isolated by filtration. Compound XIV is then added to a primary amine of general formula R2-NH$_2$ in an inert solvent (e.g., toluene) and the mixture is heated to reflux. The solvents are subsequently removed under vacuum to obtain the crude a-hydroxy-imine (XV). This intermediate is then heated, typically in a high-boiling solvent like decalin, wherein the compound undergoes a thermal rearrangement to produce the α-amino-ketone (II).

Specifically, the compound II in which X is 2-chloro, Y is hydrogen, R1 is hydrogen and R2 is methyl is commonly referred to as ketamine.

The compounds of the present invention may have optical centers denoted as "a" and "b" in the preceding schemes and therefore may occur in different enantiomeric configurations. Formula I, as depicted above, includes all enantiomers, diastereomers and other stereoisomers of the compounds depicted in structural formula I, as well as racemic and other mixtures thereof. Individual isomers can be obtained by known methods, such as optical resolution, optically selective reaction, or chromatographic separation in the preparation of the final product or its intermediate(s).

Where cis- and trans-isomers are possible (i.e., at positions "a" and "b" in structural formula I) for an embodiment of the inventive compounds of formula I, both cis- and trans-isomers (i.e., diastereomers) are within the scope of this invention.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, phosphorus, fluorine and chlorine, such as $^2$H, $^3$H, $^{11}$C, $^{13}$C, $^{13}$N, $^{15}$N, $^{18}$O, $^{35}$S, $^{31}$P, $^{18}$F and $^{37}$Cl, respectively.

Compounds of the present invention, prodrugs thereof, and pharmaceutically acceptable salts of said compounds, or of said prodrugs which contain the aforementioned isotopes and/or other isotopes of other atoms are within the scope of this invention. Certain isotopically labeled compounds of the present invention, for example, those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increases in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labeled reagent.

The term "alkyl" refers to straight or branched chains of carbon atoms. Exemplary alkyl groups are $C_3$-$C_{10}$ alkyl groups which may include methyl, ethyl, propyl, isopropyl, butyl, isobutyl, pentyl, isopentyl, hexyl and the like, including all regioisomeric forms thereof, and straight and branched chain forms thereof. The tern "alkyl" is also used to denote straight or branched chains of carbon atoms having one or more carbon—carbon double bonds, such as vinyl, allyl, butenyl and the like, as well as straight and branched chains of carbon atoms having one or more carbon-carbon triple bonds, such as ethynyl, propargyl, butynyl and the like.

The term "aryl" denotes a cyclic, aromatic hydrocarbon. Examples include phenyl, naphthyl, anthracenyl, phenanthracenyl. Such aryl groups may further be substituted at available positions with H, F, Cl, Br, I, CN, OH, alkoxy, $NO_2$, $NH_2$, NH-alkyl or N,N-dialkyl.

The terms "alkoxy" and "aryloxy" denote "O-alkyl" and "O-aryl", respectively. The term "cycloalkyl" denotes a cyclic group of carbon atoms, where the ring formed by the carbon atoms may be saturated or may comprise one or more carbon double bonds in the ring. Examples of cycloalkyl groups include cyclopropyl, cyclobutyl, cyclopentyl, cyclohexyl, cycloheptyl and the like, as well as cyclopentenyl, cyclopentadienyl, cyclohexenyl, cyclohexadienyl, and the like. As used herein, the term "cycloalkyl" is also intended to denote a cyclic group comprising at least two fused rings such as adamantyl, decahyronaphthalinyl, norbornanyl, where the cyclic group may have one or more carbon-carbon double bonds in one or more rings, such as in bicyclo(4.3.0) nona-3,6(1)-dienyl, dicyclopentadienyl, 1,2,3,4-tetrahydronaphthalinyl (i.e., tetralinyl), indenyl and the like.

The term "halogen" represents chloro, fluoro, bromo and iodo.

The term "heteroaryl" denotes a monocyclic or bicyclic aromatic group wherein one or more carbon atoms are replaced with heteroatoms selected from the group consisting of nitrogen, oxygen and sulfur. If the heteroaryl group contains more than one heteroatom, the heteroatoms may be the same or different. Preferred heteroaryl groups are five- to fourteen-member rings that contain from one to three heteroatoms independently selected from oxygen, nitrogen and sulfur. Examples of preferred heteroaryl groups include, but are not limited to benzo[b]thienyl, chromenyl, furyl, imidazolyl, indazolyl, indolizinyl, indolyl, isobenzofuranyl, isoindolyl, isoquinolinyl, isothiazolyl, isoxazolyl, naphthylidinyl, oxadiazolyl, oxazinyl, oxazolyl, phthalazinyl, pteridinyl, purinyl, pyranyl, pyrazinyl, pyrazolyl, pyridinyl, triazolyl and tetrazolyl, and said heteroaryl groups may be further substituted as described above in the definition of aryl.

A "unit dosage form" as used herein is any form that contains a unit dose of the compound I. A unit dosage form may be, for example, in the form of a tablet or a capsule. The unit dosage form may also be in a liquid form, such as a solution or suspension.

The compositions of the present invention may be formulated in a conventional manner using one or more pharmaceutically acceptable carriers. Thus, the active compounds of the present invention may be formulated for oral, buccal, intranasal, parenteral (e.g., intravenous, intramuscular or subcutaneous) or rectal administration or in a form suitable for administration by inhalation or insufflations.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose), fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia). Non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispensing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration by inhalation, the active compounds of the invention are conveniently delivered in the form of a solution or suspension from a pump spray container that is squeezed or pumped by the patient or as an aerosol spray presentation from a pressurized container or nebulizer, with the use of a suitable propellant, e.g., dichlorodifluoromethane, trichloro-fluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insulator may be formulated containing a powder mix of a compound of the invention and a suitable powder base such as lactose or starch.

A proposed dose of the active compounds of the invention for oral, parental or buccal administration to the average adult human for the treatment of the conditions referred to above is from about 0.1 mg/kg to about 100 mg/kg of the active ingredient per unit dose which could be administered, for example, one to four times per day. Toxicity concerns at the higher level may restrict intravenous (i.v.) dosage to a lower level, such as up to 10 mg/kg. A dose of about 0.1 mg/kg to about 100 mg/kg may be employed for oral (p.o.) administration. Typically, a dosage from about 0.1 mg/kg to about 10 mg/kg may be employed for intramuscular (i.m.) injection. Preferred dosages are in the 1.0 mg/kg to about 100 mg/kg range, and, more preferably in the 5 mg/kg to about 50 mg/kg range for i.v. or p.o. administration. The duration of the treatment is usually once per day for a period of one day to three weeks, or until the condition is essentially brought under control.

Aerosol formulation for treatment of the conditions referred to above in the average human are preferably arranged such that each metered dose or "puff" of aerosol contains 0.1 micrograms to 100 micrograms of the active compound of the invention. The overall daily dose with an aerosol will be within the range of 0.1 mg/kg to about 100 mg/kg, and preferably in the range of 1.0 mg/kg to about 25 mg/kg. Administration may be several times daily, for example two, three, four or eight times, giving for example one, two or three doses each time.

As an example, the mammal in need of treatment or prevention may be a human. As another example, the mammal in need of treatment or prevention may be a mammal other than a human.

A compound of formula I which is basic in nature is capable of forming a wide variety of different salts with various inorganic and organic acids. The acid addition salts are readily prepared by treating the base compounds with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid salts of the active compound used in formulating the pharmaceutical composition of this invention that are basic in nature are those which form non-toxic acid addition salts, e.g., salts containing pharmaceutically acceptable anions. Non-limiting examples of the salts include the acetate, benzoate, beta-hyroxybutyrate, bisulfate, bisulfite, bromide, butyne-1,4-dioate, caproate, chloride, chlorobenzoate, citrate, dihydrogen phosphate, dinitrobenzoate, fumarate, glycollate, heptanoate, hexyne-1,6-dioate, hydroxybenzoate, iodide, lactate, maleate, malonate, mandelate, metaphosphate, methanesulfonate, methoxybenzoate, monohydrogen phosphate, naphthalene-1-sulfonate, naphthalene-2-sulfonate, oxalate, phenylbutyrate, phenylpropionate, phosphate, phthalate, phenylacetate, propanesulfonate, propiolate, propionate, pyrophosphate, pyrosulfate, sebacate, suberate, succinate, sulfate, sulfite, sulfonate, tartrate, xylenesulfonate, acid phosphate, acid citrate, bitartrate, succinate, gluconate, saccharate, nitrate, methanesulfonate and pamoate (i.e., 1,1'-methylene-bis-(2-hydroxy-3-naphthoate) salts.

Also included within the scope of this invention are solvates and hydrates of compounds of formula I and their pharmaceutically acceptable salts. The present invention includes within its scope all possible stoichiometric and non-stoichiometric forms.

In the examples that follow, the abbreviations used in this document are intended to have the following, general meaning:

bm: broad multiplet (NMR)
bs; broad singlet (NMR)
d: doublet (NMR
dd: doublet of doublets (NMR)
d.e. diatomaceous earth, a filtering agent
calc.: calculated value
J: coupling constant (NMR)
LC: liquid chromatography
m: multiplet (NMR)
min: minute(s)
m/z: mass to charge ratio (mass spectroscopy)
obsd: observed value
Rf: retention factor or ratio
RT: retention time
RT: room temperature (typically 25° C.)
s: singlet (NMR)
t: triplet (NMR)
T: temperature
tlc: thin layer chromatography Solvents were purchased and used without purification. Yields were calculated for material judged to be homogeneous by thin layer chromatography and NMR.

Thin-layer chromatography was performed on Kieselgel plates eluting with the indicated solvents, visualized by using a 254 nm UV lamp, and stained with an iodo-platinate spray solution (Sigma Aldrich Chemical Co.).

Preparatory chromatography was performed on Analtech Preparative Uniplates (20×20 cm, 2000 mm thick, UV, Silica G) purchased from ColeParmer, Vernon Hills, Ill. 60061, eluting with the indicated solvents and visualized by using a 2554 nm UV lamp.

Liquid chromatography was performed using a Teledyne-Isco CombiFlash Rf+ Lumen instrument with RediSep Rf High Performance Gold 12-, 24-, or 40-gram, 40-60 micron silica gel, disposable flash columns (Teledyne Instruments, Chicago, Ill. and Teledyne ISCO, Lincoln, Nebra.

Nuclear Magnetic Resonance (NMR) spectra were acquired on either a 400 MHz or an 800 MHz Varian NMR Spectrometer (Varian Inc., Palo Alto, Calif.). Chemical shifts for hydrogen, carbon and nitrogen (i.e., $^1H$, $^{13}C$, $^{15}N$) NMR spectra are reported in parts per million (ppm) relative to the singlet for $CDCl_3$ at 7.23 ppm.

Mass Spectrometry data were obtained on an Advion Expressions CMS (Advion Inc., Ithaca, N.Y. 14850) in the mass range of 100-800 Daltons.

EXPERIMENTAL SECTION

Example 1

Resolution of Racemic (R,S)-Ketamine

Step 1: Preparation of the L-DPPTA Salts of S-(+)-Ketamine and R-(−)-Ketamine

A 50 mL round-bottom flask fitted with a water condenser and magnetic stir bar was charged with 2.8503 g (12.0 mmol) of racemic ketamine free base (isolated from the hydrochloride salt purchased from Spectrum Chemical Mfg. Corp., Los Angeles, Calif.). Absolute ethanol (14.0 mL, Sigma-Aldrich, Inc., St. Louis, Mo.) was added and the stirred slurry was treated with (−)-di-p-toluoyl-L-tartaric acid (L-DPPTA, 4.62323 g, 12.00 mmol, MW 386.36, Sigma-Aldrich) at room temperature. The resulting thick slurry was heated with an oil bath at 84° C. to a water white solution. After removal of the heat, the reaction was allowed to cool to 28° C. (bath temp.) and was seeded with S-ketamine L-(−)-DPPTA salt (from a previous preparation). After stirring at rt overnight, the flask was cooled with an ice bath and the white solids were filtered, washed with a small amount of ice-cold ethanol, dried under vacuum and transferred to a tared flask. The resulting white solid, 1A, 3.3381 g (Yield=89%) of the L-DPPTA salt of (S)-ketamine had a specific rotation $[\alpha]_D$=−128° (c=1, T=21° C., DMF).

The filtrate was transferred to a round-bottom flask and concentrated in vacuo to a white solid. This was treated with 7.5 mL of acetonitrile and heated with a condenser and oil bath to 85° C. The resulting slurry was treated with a total of 6.7 mL of methanol. The resulting homogeneous solution was allowed to slowly stir while cooling to room temperature overnight, creating a white slurry which was further cooled in an ice bath. The solids were filtered, washed with a small amount of acetonitrile followed by a small amount of methyl tert-butyl ether. The solids were transferred to a tared flask and dried under vacuum to a white solid. The resulting white solid, 1B, 2.6313 g (yield=70%) of he (L)-DPPTA salt of (R)-ketamine had a specific rotation $[\alpha]_D$=−28° (c=1, T=21° C., DMF).

Step 2: Preparation of the Free Base of S-(+)-Ketamine and R-(−)-Ketamine

A mixture of 9.0769 g (14.5 mmol) of (S)-Ketamine salt 1B, 58.4 ml water and 63.5 mL toluene was stirred in a 250 mL round-bottom flask while adding 32 mL of 1N NaOH. After 20 min. the mixture was transferred to a separatory funnel, the organic layer was combined with 2×63 mL extractions of the aqueous layer. The organic layers were washed 2×50 mL water, dried over $Na_2SO_4$, filtered and concentrated in vacuo. The residue was azeotroped in vacuo with methanol and the remaining oil was treated with ethanol to precipitating a white solid. Removal of the remaining methanol in vacuo resulted in pure (S)-ketamine free base a s white granular solid, 1a, 3.2915 g, 95.46%.

$[\alpha]_D^{223°}$ C.=−55°, in 2% ethanol,
Mass spectrum: [M+]=238
M.P.=120-121° C.

In the same manner, 2.5 g (4.01 mmol) of the (R)-Ketamine salt 1b was converted to the free base 1 b as a white solid, 0.9452 g (99.3%),
$[\alpha]_D^{22.3°}$ C.=−+54°, in 2% ethanol.

Example 2

Cis-(1S,2S)-1-(2-chlorophenyl)-$N^1$-methyl-$N^2$-[3-(pyrrolidin-1-yl)propyl]-cyclohexane-1,2-diamine trihydrochloride (2a, Cis-); and Trans-(1S,2R)-1-(2-chlorophenyl)-$N^1$-methyl-$N^2$-[3-(pyrrolidin-1-yl)propyl]-cyclohexane-1,2-diamine trihydrochloride (2b, Trans-)

A 50 mL round-bottom flask fitted with a water condenser and magnetic stir bar was charged with 0.5009 g (1.827 mmol) of S-(+)-ketamine hydrochloride 1a (Sigma-Aldrich, Inc) and 15 mL of absolute ethanol. While stirring, 0.7 mL (MW=128.2, d=1.014 g/ml) of 1-(3-aminopropyl)pyrrolidine (Tokyo Chemical Industry—TCI America, Portland, Oreg.) was added, followed by 1.1 mL (MW=284.2, d=0.96 g/mL) of titanium (IV) isopropoxide (TCI America). The reactants were heated to reflux overnight. After 24 hr., an additional 0.54 mL of titanium (IV) isopropoxide was added and reflux was continued overnight. The reaction was then allowed to cool to room temperature at which point 138.2 mg of sodium borohydride in 8.0 mL of anhydrous ethanol was slowly added with stirring. The reaction was then treated with 13 mL of 1N HCl to a pH of 2.0. The resulting milky white slurry was transferred to a 250 mL round-bottom flask. Ethyl acetate (32 mL) was added and the pH readjusted to 10-11 with 1N NaOH (15 mL). This mixture was filtered through diatomaceous earth (d.e.), washing the cake with 2×10 mL EtOAc. The filtrate was transferred to a separatory funnel, 20 mL of saturated aqueous NaCl was added and the organic layer was isolated.

The organic layer was absorbed onto 2.6 g of silica gel 60A (Sigma-Aldrich Co.) and this was processed on a Teledyne-Isco CombiFlash Rf+ Lumen through a RediSep Rf High Performance Gold (40-gram, 40-60 micron silica) disposable flash column using 50% EtOAc: 50% IPO: 1.5-5.0% triethylamine as the mobile phase.

The less polar (LP) fractions 12-15 and the more polar (MP) fractions 18-22 were isolated and separately concentrated in vacuo.

The LP fractions produced 100.9 mg of colorless oil (trans-isomer). $^1$H-NMR (400 MHz, $CDCl_3$) was consistent for the product. The oil was dissolved in EtOAc and treated with 3.3 equivalents of 2M HCl in $Et_2O$) (Sigma-Aldrich) with stirring to precipitate the HCl salt as a white solid, 2b, 0.1376 g. Mass spectrum calculated for $C_{13}H_{16}ClNO$: m/e 352, 350 ([M+H]+, 20%), 321, 319 (100%).

The MP fractions produced 258.6 mg of a colorless oil (cis-isomer). $^1$H-NMR (400 MHz, $CDCl_3$) was consistent for the product. The oil was similarly dissolved in EtOAc and treated with 3.3 equivalents of 2M HCl in $Et_2O$ to precipitate the HCl salt as a white solid, 2a, 0.2860 g. Mass spectrum calculated for $C_{13}H_{16}ClFNO$: m/e 352, 350 ([M+H]+, 100%), 321, 319 (20%).

Example 3

Cis-(1S,2S)-1-(2-chlorophenyl)-$N^2$-[3-(4-fluorophenyl)propyl]-$N^1$-methylcyclohexane-1,2-diamine dihydrochloride (3a, Cis-); and Trans-(1S,2R)-1-(2-chlorophenyl)-$N^2$-[3-(4-fluorophenyl)propyl]-$N^1$-methylcyclohexane-1,2-diamine dihydrochloride (3b, Trans-)

Using a similar procedure to that of Example 2, 89.5 mg of (S)-ketamine 1a and 100 mg of 3-(4-fluorophenyl)propylamine (Sigma-Aldrich Co) were converted to the corresponding cis- and trans-diastereomers, 3a and 3b as solid white dihydrochloride salts.

3a: 37.5 mg (61%). Mass spectrum calculated for $C_{22}H_{28}ClFN_2$: m/e 377, 375 ([M+H]+, 65%), 346, 344 (100%).

3b: 37.6 mg (61%). Mass spectrum calculated for $C_{22}H_{28}ClFN_2$: m/e 377, 375 ([M+H]+, 20%), 346, 344 (100%).

Example 4

Cis-(1S,2S)-1-(2-chlorophenyl)-$N^1$-methyl-$N^2$-(3-phenylpropyl)cyclohexane-1,2-diamine dihydrochloride (4a, Cis-); and Trans-(1S,2R)-1-(2-chlorophenyl)-$N^1$-methyl-$N^2$-(3-phenylpropyl)cyclohexane-1,2-diamine dihydrochloride (4b, Trans-)

Using a similar procedure to that of Example 2, 300 mg (1.094 mmol) of (S)-ketamine 1a and 0.31 mL of 3-phenyl- 1-propylamine (Sigma-Aldrich Co) were converted to the corresponding cis- and trans-diastereomers, 4a and 4b as solid white dihydrochloride salts.

4a: 161.4 mg (69%). Mass spectrum calculated for $C_{22}H_{29}ClN_2$: m/e 359, 357 ([M+H]+, 100%), 328, 326 (80%).

4b: 81.4 mg (35%). Mass spectrum calculated for $C_{22}H_{29}ClN_2$: m/e 359, 357 ([M+H]+, 25%), 328, 326 (100%).

Example 5

Cis-(1S,2S)-1-(2-chlorophenyl)-$N^2$-[3,4-dimethoxyphenethyl]-$N^1$-methylcyclohexane-1,2-diamine dihydrochloride (5a, Cis-)

Trans-(1S,2R)-1-(2-chlorophenyl)-$N^2$-[3,4-dimethoxyphenethyl]-$N^1$-methylcyclohexane-1,2-diamine dihydrochloride (5b, Trans-)

Using a similar procedure to that of Example 2, 300 mg (1.094 mmol) of (S)-ketamine 1a and 3,4-dimethoxy-phenethylamine (TCI) were converted to the corresponding cis- and trans-diastereomers, 5a and 5b as solid white dihydrochloride salts.

5a: 123.3 mg (28%). Mass spectrum calculated for $C_{23}H_{31}ClN_2O_2$: m/e 405, 403 ([M+H]+, 60%), 374, 372 (100%).

5b: 106.3 mg (24.5%). Mass spectrum calculated for $C_{23}H_{31}ClN_2O_2$: m/e 405, 403 ([M+H]+, 10%), 374, 372 (100%).

Example 6

Cis-(1S,2S)-1-(2-chlorophenyl)-$N^1$-methyl-$N^2$-(3-morpholinopropyl)cyclohexane-1,2-diamine trihydrochloride (6a, Cis-); and Trans-(1S,2R)-1-(2-chlorophenyl)-$N^1$-methyl-$N^2$-(3-morpholinopropyl)cyclohexane-1,2-diamine trihydrochloride (6b, Trans-)

Using a similar procedure to that of Example 2, 300 mg (1.094 mmol) of (S)-ketamine 1a and 3-aminopropyl-morpholine (TCI) were converted to the corresponding cis- and trans-diastereomers, 6a and 6b as solid white trihydrochloride salts.

6a: 75.4 mg (21.7%). Mass spectrum calculated for $C_{20}H_{32}ClN_3O$: m/e 368, 366 ([M+H]+, 100%), 337, 335 (20%).

6b: 124.9 mg (36%). Mass spectrum calculated for $C_{20}H_{32}ClN_3O$: m/e 368, 366 ([M+H]+, 10%), 337, 335 (100%).

Example 7

Cis-(1R,2S)—$N^2$-benzyl-1-(2-chlorophenyl)-$N^1$-methylcyclohexane-1,2-diamine dihydrochloride (7a, Cis-); and Trans-(1R,2R)—$N^2$-benzyl-1-(2-chlorophenyl)-$N^1$-methylcyclohexane-1,2-diamine dihydrochloride (7b, Trans-)

Using a similar procedure to that of Example 2, 300 mg of (R)-ketamine 1b and benzylamine (TCI) were converted to the corresponding cis- and trans-diastereomers, 7a and 7b as solid white dihydrochloride salts.

7a: 89.8 mg (35%). Mass spectrum calculated for $C_{20}H_{25}ClN_2$: m/e 331, 329 ([M+H]+, 5%), 300, 298 (100%).

7b: 46.3 mg (18%). Mass spectrum calculated for $C_{20}H_{25}ClN_2$: m/e 331, 329 ([M+H]+, 10%), 300, 298 (100%).

Example 8

Cis-(1S,2R)—$N^2$-benzyl-1-(2-chlorophenyl)-$N^1$-methylcyclohexane-1,2-diamine dihydrochloride (8a, Cis-); and Trans-(1S,2S)—$N^2$-benzyl-1-(2-chlorophenyl)-$N^1$-methylcyclohexane-1,2-diamine dihydrochloride (8b, Trans-)

Using a similar procedure to that of Example 2, 300 mg (1.094 mmol) of (S)-ketamine 1a and benzylamine (TCI) were converted to the corresponding cis- and trans-diastereomers, 8a and 8b as solid white dihydrochloride salts.

8a: 58.3 mg (19.8%). Mass spectrum calculated for $C_{20}H_{25}ClN_2$: m/e 331, 329 ([M+H]+, 125%), 300, 298 (100%).

8b: 109.9 mg (38%). Mass spectrum calculated for $C_{20}H_{25}ClN_2$: m/e 331, 329 ([M+H]+, 10%), 300, 298 (100%).

Example 9

Cis-(1R,2S)-1-(2-chlorophenyl)-$N^1$-methyl-$N^2$-(3-(pyrrolidin-1-yl)propyl)-cyclohexane-1,2-diamine trihydrochloride (9a, Cis-); and Trans-(1R,2R)-1-(2-chlorophenyl)-$N^1$-methyl-$N^2$-(3-(pyrrolidin-1-yl)propyl)-cyclohexane-1,2-diamine trihydrochloride (9b, Trans-)

Using a similar procedure to that of Example 2, 300 mg (1.094 mmol) of (R)-ketamine 1a and 3-(aminopropyl-pyrrolidine (TCI) were converted to the corresponding cis- and trans-diastereomers, 9a and 9b as solid white trihydrochloride salts.

9a: 165.3 mg (21.7%). Mass spectrum calculated for $C_{20}H_{32}ClN_3$: m/e 352, 350 ([M+H]+, 100%), 321, 319 (20%).

9b: 35 mg (6%). Mass spectrum calculated for $C_{20}H_{32}ClN_3$: m/e 352, 350 ([M+H]+, 45%), 321, 319 (100%).

Example 10

Cis-(1R,2S)-1-(2-chlorophenyl)-$N^2$-[3,4-dimethoxyphenethyl]-$N^1$-methyl-cyclohexane-1,2-diamine dihydrochloride (10a, Cis-); and Trans-(1R,2R)-1-(2-chlorophenyl)-$N^2$-[3,4-dimethoxyphenethyl]-$N^1$-methyl-cyclohexane-1,2-diamine dihydrochloride (10b, Trans-)

Using a similar procedure to that of Example 2, 300 mg (1.094 mmol) of (R)-ketamine 1a and homoveratrylamine (TCI) were converted to the corresponding cis- and trans-diastereomers, 10a and 10b as solid white dihydrochloride salts.

10a: 58.2 mg (21%). Mass spectrum calculated for $C_{23}H_{31}ClN_2O_2$: m/e 405, 403 ([M+H]+, 35%), 374, 372 (100%).

10b: 33.9 mg (12%). Mass spectrum calculated for $C_{23}H_{31}ClN_2O_2$: m/e 405, 403 ([M+H]+, 8%), 374, 372 (100%).

Example 11

Cis-(1 S,2S)-1-(2-chlorophenyl)-$N^2$-[3,4-dichlorobenzyl]-$N^1$-methyl-cyclohexane-1,2-diamine dihydrochloride (11a, Cis-); and Trans-(1S,2R)-1-(2-chlorophenyl)-$N^2$-[3,4-dichlorobenzyl]-$N^1$-methyl-cyclohexane-1,2-diamine dihydrochloride (11b, Trans-)

Using a similar procedure to that of Example 2, 300 mg (1.094 mmol) of (S)-ketamine 1a and 3,4-dichlorobenzylamine (TCI) were converted to the corresponding cis- and trans-diastereomers, 11a and 11b as solid white dihydrochloride salts.

11a: 26.3 mg (6%). Mass spectrum calculated for $C_{20}H_{23}Cl_3N_2$: m/e 401, 399, 397 ([M+H]+, 7%), 370, 368, 366 (100%).

11b: 51.4 mg (12%). Mass spectrum calculated for $C_{20}H_{23}ClN_2$: m/e 401, 399, 397 ([M+H]+, 5%), 370, 368, 366 (100%).

Example 12

Cis-(1S,2S)—$N^2$-(3-aminopropyl)-1-(2-chlorophenyl)-$N^1$-methylcyclohexane-1,2-diamine trihydrochloride (12a, Cis-); and Trans-(1S,2R)—$N^2$-(3-aminopropyl)-1-(2-chlorophenyl)-$N^1$-methylcyclohexane-1,2-diamine trihydrochloride (12b, Trans-)

Using a similar procedure to that of Example 2, 300 mg (1.094 mmol) of (S)-ketamine 1a and 1,3-diaminopropane (TCI) were converted to the corresponding cis- and trans-diastereomers, 12a and 12b as solid white trihydrochloride salts.

12a: 81.7 mg (27%). Mass spectrum calculated for $C_{16}H_{26}ClN_3$: m/e 298, 296 ([M+H]+, 10%), 267, 265 (100%).

12b: 62.9 mg (21%). Mass spectrum calculated for $C_{16}H_{26}ClN_3$: m/e 298, 296 ([M+H]+, 45%), 267, 265 (100%).

Example 13

Cis-(1S,2S)-1-(2-chlorophenyl)-$N^1$-methyl-$N^2$-(3-(4-methylpiperazin-1-yl)-propyl)cyclohexane-1,2-diamine tetrahydrochloride (13a, Cis-); and Trans-(1S,2R)-1-(2-chlorophenyl)-$N^1$-methyl-$N^2$-(3-(4-methylpiperazin-1-yl)-propyl)cyclohexane-1,2-diamine tetrahydrochloride (13b, Trans-)

Using a similar procedure to that of Example 2, 300 mg (1.094 mmol) of (S)-ketamine 1a and 3-(4-methylpiperazin-1-yl)propan-1-amine (Combi-Blocks, Inc., San Diego, Calif.) were converted to the corresponding cis- and trans-diastereomers, 13a and 13b as solid white tetrahydrochloride salts.

13a: 267 mg (76%). Mass spectrum calculated for $C_{21}H_{35}ClN_4$: m/e 381, 379 ([M+H]+, 100%), 350, 348 (15%).

13b: 121.4 mg (35%). Mass spectrum calculated for $C_{21}H_{35}ClN_4$: m/e 381, 379 ([M+H]+, 35%), 350, 348 (100%).

Determination of Pharmacological Activity

The compounds from the above Examples were tested for Sigma-1 and Sigma-2 activity. Ki determinations were generously provided by the National Institute of Mental Health's Psychoactive Drug Screening Program (PDSP), Contract #HHSN-272-2013-000017-C (NIMH-PDSP). The NIMH-PDSP is directed by Bryan L Roth M D, PhD at the University of North Carolina at Chapel Hill, N.C. and Project Officer Jamie Driscoll at NIMH, Bethesda, Md., USA. Procedures employed by the PDSP are described in the NIMH-PDSP Assay Protocol Book, Version II. The standard drug used in both Sigma subtype assays is haloperidol.

Data

| Example | Sigma-1, Ki (nM) | Sigma-2, Ki, (nM) |
| --- | --- | --- |
| 2a | 17.3 | 59.8 |
| 2b | 37.2 | 305 |
| 3a | 35.4 | 18 |
| 3b | 216.7 | 675 |
| 4a | 97.2 | 15.5 |
| 4b | 697 | 425.7 |
| 13a | 70 | 98 |
| 13b | 146 | 435 |

The invention claimed is:
1. A method of treatment of an inflammatory disorder or condition resulting from a bacterial or viral infection in a mammal, the method comprising administering to a mammal in need of such treatment a therapeutically effective amount of a compound of the formula (I):

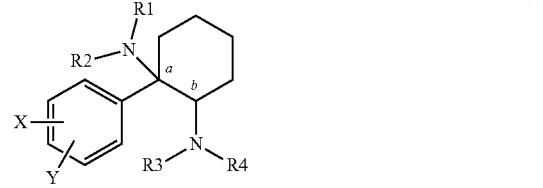

or a pharmaceutically acceptable salt thereof, wherein:
X and Y are independently selected from the group consisting of H, F, Cl, Br, I, CN, OH, $CF_3$, $C_2F_5$, $C_1$-$C_6$-alkyl, $C_3$-$C_7$-cycloalkyl, $C_1$-$C_3$-alkoxy, aryl, heteroaryl, —(C═O)—R5, —NH—(C═O)—R5, —NR5—(C═O)—R6, —(C═O)—NHR5 and —(C═O)—NR5R6;
R1 is hydrogen;
R2 is hydrogen or $C_1$-$C_6$-alkyl;
R3 is hydrogen or $C_1$-$C_6$-alkyl;
R4 is selected from the group consisting of $C_1$-$C_6$-alkyl, $C_3$-$C_7$-cycloalkyl and $(CH_2)_n$—R7, or NR3N4 is a 5- to 12-membered cyclic or bicyclic ring system containing up to two additional heteroatoms in the ring, selected from N, O and S;

R5 is selected from $C_1$-$C_6$-alkyl and aryl;

R6 is selected from $C_1$-$C_6$-alkyl and aryl;

NR5R6 is a 5- to 12-membered cyclic or bicyclic ring system containing up to two additional heteroatoms in the ring, selected from N, O and S;

R7 is independently selected from the group consisting of H, $C_1$-$C_6$-alkyl, $C_3$-$C_7$-cycloalkyl, ($C_1$-$C_6$-alkoxy)-, ($C_1$-$C_6$-alkoxy)-($C_1$-$C_6$-alkyl), NR8R9, NR8R9-($C_1$-$C_6$-alkyl), aryl, heterocyclyl and heteroaryl;

R8 and R9 are independently selected from hydrogen, $C_1$-$C_6$-alkyl and aryl, or taken together with the N atom to which they are attached form a 3- to 8-membered ring containing up to two additional heteroatoms, selected from N, O and S;

"a" and "b" are chiral carbon atoms; and n is an integer between 0 and 6.

2. The method of claim 1 wherein R4 is $C_1$-$C_6$-alkyl, $C_3$-$C_7$-cycloalkyl or $(CH_2)_n$—R7 and wherein n is an integer between 0 and 6.

3. The method of claim 1 wherein R7 is selected from the group consisting of H, $C_1$-$C_6$-alkyl, $C_3$-$C_7$-cycloalkyl, ($C_1$-$C_6$-alkyloxy)-($C_1$-$C_6$-alkyl)-, NR8R9-($C_1$-$C_6$-alkyl)-, aryl, heterocyclyl and heteroaryl.

4. The method of claim 1 wherein said compound is selected from:

Cis-(1S,2S)-1-(2-chlorophenyl)-$N^1$-methyl-$N^2$-[3-(pyrrolidin-1-yl)propyl]-cyclohexane-1,2-diamine trihydrochloride;

Trans-(1S,2R)-1-(2-chlorophenyl)-$N^1$-methyl-$N^2$-[3-(pyrrolidin-1-yl)propyl]-cyclohexane-1,2-diamine trihydrochloride;

Cis-(1S,2S)-1-(2-chlorophenyl)-$N^2$-[3-(4 fluorophenyl)propyl]-$N^1$-methylcyclohexane-1,2-diamine dihydrochloride;

Trans-(1S,2R)-1-(2-chlorophenyl)-$N^2$-[3-(4-fluorophenyl)propyl]-$N^1$-methylcyclohexane-1,2-diamine dihydrochloride;

Cis-(1S,2S)-1-(2-chlorophenyl)-$N^1$-methyl-$N^2$-(3-phenylpropyl)cyclohexane-1,2-diamine dihydrochloride;

Trans-(1S,2R)-1-(2-chlorophenyl)-$N^1$-methyl-$N^2$-(3-phenylpropyl)cyclohexane-1,2-diamine dihydrochloride;

Cis-(1S,2S)-1-(2-chlorophenyl)-$N^2$-(3,4-dimethoxyphenethyl)-$N^1$-methylcyclohexane-1,2-diamine dihydrochloride;

Trans-(1S,2R)-1-(2-chlorophenyl)-$N^1$-(3,4-dimethoxyphenethyl)-$N^1$-methylcyclohexane-1,2-diamine dihydrochloride;

Cis-(1S,2S)-1-(2-chlorophenyl)-$N^1$-methyl-$N^2$-(3-morpholinopropyl)cyclohexane-1,2-diamine trihydrochloride;

Trans-(1S,2R)-1-(2-chlorophenyl)-$N^1$-methyl-$N^2$-(3-morpholinopropyl)cyclohexane-1,2-diamine trihydrochloride;

Cis-(1R,2S)—$N^2$-benzyl-1-(2-chlorophenyl)-$N^1$-methylcyclohexane-1,2-diamine dihydrochloride;

Trans-(1R,2R)—$N^2$-benzyl-1-(2-chlorophenyl)-$N^1$-methylcyclohexane-1,2-diamine dihydrochloride;

Cis-(1S,2R)—$N^2$-benzyl-1-(2-chlorophenyl)-$N^1$-methylcyclohexane-1,2-diamine dihydrochloride;

Trans-(1S,2S)—$N^2$-benzyl-1-(2-chlorophenyl)-$N^1$-methylcyclohexane-1,2-diamine dihydrochloride;

Cis-(1R,2S)-1-(2-chlorophenyl)-$N^1$-methyl-$N^2$-[3-(pyrrolidin-1-yl)propyl]-cyclohexane-1,2-diamine trihydrochloride;

Trans-(1R,2R)-1-(2-chlorophenyl)-$N^1$-methyl-$N^2$-[3-(pyrrolidin-1-yl)propyl]-cyclohexane-1,2-diamine trihydrochloride;

Cis-(1R,2S)-1-(2-chlorophenyl)-$N^2$-(3,4-dimethoxyphenethyl)-$N^1$-methylcyclohexane-1,2-diamine dihydrochloride;

Trans-(1R,2R)-1-(2-chlorophenyl)-$N^2$-(3,4-dimethoxyphenethyl)-$N^1$-methyl-cyclohexane-1,2-diamine dihydrochloride;

Cis-(1S,2S)-1-(2-chlorophenyl)-$N^2$-(3,4-dichlorobenzyl)-$N^1$-methylcyclohexane-1,2-diamine dihydrochloride;

Trans-(1S,2R)-1-(2-chlorophenyl)-$N^2$-(3,4-dichlorobenzyl)-$N^1$-methylcyclohexane-1,2-diamine dihydrochloride;

Cis-(1S,2S)—$N^2$-(3-aminopropyl)-1-(2-chlorophenyl)-$N^1$-methylcyclohexane-1,2-diamine trihydrochloride;

Trans-(1S,2R)—$N^2$-(3-aminopropyl)-1-(2-chlorophenyl)-$N^1$-methylcyclohexane-1,2-diamine trihydrochloride;

(1S,2S)-1-(2-chlorophenyl)-$N^1$-methyl-$N^2$-(3-(4-methylpiperazin-1-yl)propyl)-cyclohexane-1,2-diamine tetrahydrochloride; and (1S,2R)-1-(2-chlorophenyl)-$N^1$-methyl-$N^2$-(3-(4-methylpiperazin-1-yl)propyl)-cyclohexane-1,2-diamine tetrahydrochloride.

5. The method of claim 1 wherein said compound is selected from:

(1R,2S)-1-(2-chlorophenyl)-$N^1$-methyl-$N^2$-(3-(pyrrolidin-1-yl)propyl)cyclohexane-1,2-diamine;

(1R,2S)—$N^2$-(3-(1H-pyrrol-1-yl)propyl)-1-(2-chlorophenyl)-$N^1$-methylcyclohexane-1,2-diamine;

(1R,2S)-1-(2-chlorophenyl)-$N^1$-methyl-$N^2$-(3-(2-methyl-1H-imidazol-1-yl)propyl)cyclohexane-1,2-diamine;

(1R,2S)-1-(2-chlorophenyl)-$N^1$-methyl-$N^2$-(3-(4-methylpiperazin-1-yl)propyl)cyclohexane-1,2-diamine;

(1R,2S)-1-(2-chlorophenyl)-$N^1$-methyl-$N^2$-(3-morpholinopropyl)cyclohexane-1,2-diamine;

(1R,2S)-1-2-chlorophenyl)-$N^1$-methyl-$N^2$-(3-(pyrrolidin-1-yl)propyl)-cyclohexane-1,2-diamine;

(1R,2S)-1-(2-chlorophenyl)-$N^2$-(3-(dimethylamino(propyl)-$N^1$-methylcyclohexane-1,2-diamine;

(1R,2S)-1-(2-chlorophenyl)-$N^2$-(3,4-dimethylbenzyl)-$N^1$-methylcyclohexane-1,2-diamine;

(1R,2S)—$N^2$-(1-chlorobenzyl)-1-(2-chlorophenyl)-$N^1$-methylcyclohexane-1,2-diamine;

(1R,2S)-(2-chlorophenyl)-$N^2$-(3,5-difluorobenzyl)-$N^1$-methylcyclohexane-1,2-diamine;

(1R,2S)-1-(2-chlorophenyl)-$N^1$-methyl-$N^2$-(4-(trifluoromethyl)benzyl)-cyclohexane-1,2-diamine;

(1R,2S)-1-(2-chlorophenyl)-$N^1$-methyl-$N^2$-(4-((trifluoromethyl)thio)benzyl)-cyclohexane-1,2-diamine;

(1R,2S)—$N^2$-(5-chloro-2-fluorobenzyl)-1-(2-chlorophenyl)-$N^1$-methylcyclohexane-1,2-diamine;

(1R,2S)-1-(2-chlorophenyl)-$N^1$-methyl-$N^2$-(5-methoxy-2-methylbenzyl)-$N^1$-methylcyclohexane-1,2-diamine;

(1R,2S)-1-(2-chlorophenyl)-$N^1$-methyl-$N^2$-(thiazol-2-ylmethyl)cyclohexane-1,2-diamine;

(1R,2S)-1-(2-chlorophenyl)-$N^1$-methyl-$N^2$-(thiophen-3-ylmethyl)cyclohexane-1,2-diamine;

(1R,2S)-1-(2-chlorophenyl)-$N^2$-(furan-2-ylmethyl)-$N^1$-methylcyclohexane-1,2-diamine;

(1R,2S)-1-(2-chlorophenyl)-$N^1$-methyl-$N^2$-(thiophen-2-ylmethyl)cyclohexane-1,2-diamine;

(1R,2S)-1-(2-chlorophenyl)-$N^1$-methyl-$N^2$-((methyl-1H-pyrazol-4-yl)methyl)-cyclo-hexane-1,2-diamine;

(1R,2S)-1-(2-chlorophenyl)-$N^2$-(cyclobutylmethyl)-$N^1$-methylcyclohexane-1,2-diamine;

(1R,2S)-1-(2-chlorophenyl)-N²-(cyclopropylmethyl)-N¹-methylcyclohexane-1,2-diamine;
(1R,2S)-1-(2-chlorophenyl)-N¹-methyl-N²-neopentylcyclohexane-1,2-diamine;
(1R,2S)-1-(2-chlorophenyl)-N²-(2,2-difluoroethyl)-N¹-methylcyclohexane-1,2-diamine;
(1R,2S)-1-(2-chlorophenyl)-N²-(cyclopropylethyl)-N¹-methylcyclohexane-1,2-diamine;
(1R,2S)-1-(2-chlorophenyl)-N²-cyclohexylmethyl)-N¹-methylcyclohexane-1,2-diamine;
(1R,2S)-1-(2-chlorophenyl)-N¹-methyl-N²—((R)-quinuclidin-3-yl)cyclohexane-1,2-diamine;
(1R,2S)-1-(2-chlorophenyl)-N¹-methyl-N²—((S)-quinuclidin-3-yl)cyclohexane-1,2-diamine;
(1R,2S)-1-(2-chlorophenyl)-N¹-methyl-N²-(pyridine-4-ylmethyl)cyclohexane-1,2-diamine;
(1R,2S)-1-(2-chlorophenyl)-N¹-methyl-N²-(pyridine-2-ylmethyl)cyclohexane-1,2-diamine;
(1R,2S)-1-(2-chlorophenyl)-N¹-methyl-N²-(pyrimidin-2-ylmethyl)cyclohexane-1,2-diamine;
(1R,2S)-1-(2-chlorophenyl)-N¹-methyl-N²-(3-methylpyridin-4-yl)methyl)-cyclohexane-1,2-diamine;
(1R,2S)-1-(2-chlorophenyl)-N¹-methyl-N²-(pyrazin-2-ylmethyl)cyclohexane-1,2-diamine;
(1R,2S)-1-(2-chlorophenyl)-N¹-methyl-N²-(quinoline-6-ylmethyl)cyclohexane-1,2-diamine;
(1R,2S)-1-(2-chlorophenyl)-N¹-methyl-N²-((1-methyl-1H-indol-5-yl)methyl)-cyclohexane-1,2-diamine;
(1R,2S)-1-(2-chlorophenyl)-N²—((S)-1-(4-methoxyphenyl)ethyl)-N¹-methylcyclohexane-1,2-diamine;
(1R,2S)-1-(2-chlorophenyl)-N²—((R)-1-(4-methoxyphenyl)ethyl)-N¹-methylcyclohexane-1,2-diamine;
(1R,2S)-1-(2-chlorophenyl)-N¹-methyl-N²—((S)-1-phenylethyl)cyclohexane-1,2-diamine;
(1R,2S)-1-(2-chlorophenyl)-N¹-methyl-N²—((R)-1-phenylethyl)cyclohexane-1,2-diamine;
(1R,2S)-1-(2-chlorophenyl)-N¹-methyl-N²—((S)-1-(p-tolyl)ethyl)cyclohexane-1,2-diamine;
(1R,2S)-1-(2-chlorophenyl)-N¹-methyl-N²—((R)-1-(p-tolyl)ethyl)cyclohexane-1,2-diamine;
(1R,2S)-1-(2-chlorophenyl)-N¹-methyl-N²—((R)-1,2,3,4-tetrahydronaphthalen-1-yl)cyclo-hexane-1,2-diamine;
(1R,2S)-1-(2-chlorophenyl)-N¹-methyl-N²—((S)-1,2,3,4-tetrahydronaphthalen-1-yl)cyclo-hexane-1,2-diamine;
(1R,2S)-1-(2-chlorophenyl)-N¹-methyl-N²—((R)-2-(phenylpropyl)cyclohexane-1,2-diamine;
(1R,2S)-1-(2-chlorophenyl)-N¹-methyl-N²—((S)-2-(phenylpropyl)cyclohexane-1,2-diamine;
(R)-1-((1S,2R)-2-(2-chlorophenyl)-2-(methylamino)cyclohexyl)-N,N-dimethylpyrrolidin-3-amine; and
(S)-1-((1S,2R)-2-(2-chlorophenyl)-2-(methylamino)cyclohexyl)-N,N-dimethylpyrrolidin-3-amine.

6. The method of claim 1 wherein the infective agent is a bacterium.

7. The method of claim 1 wherein the infective is a virus.

8. The method of claim 1 wherein the mammal is a human.

9. The method of claim 7 wherein the virus is a novel coronavirus SARS-CoV.

10. A method of preparing a compound of formula (I) of claim 1, wherein a compound of formula (VI):

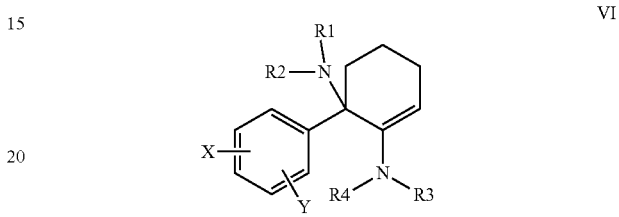

is reduced with sodium borohydride in a reaction inert solvent selected from the list consisting of methanol, ethanol and isopropanol.

11. The method of claim 10 comprising preparing a compound of formula (VI) wherein the individual R-(+)- and S-(−)-isomers of ketamine (II):

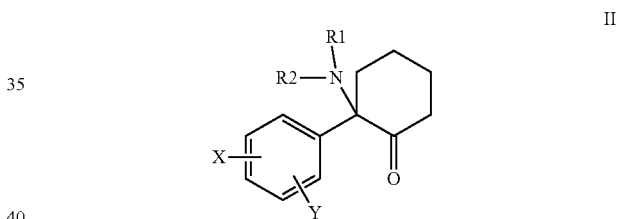

are heated in the presence of an amine of formula (V), HNR³R⁴, and titanium isopropoxide in a reaction inert solvent selected from the list consisting of methanol, ethanol and isopropanol.

12. The method of claim 11 comprising preparing the individual R-(+)- and S-(−)-isomers of ketamine (II), wherein their (+)- and (−)-di-para-toluoyl-L-tartaric acid salts are purified by crystallization and then converted to the corresponding R-(+)- and S-(+)-ketamine free bases.

* * * * *